(12) United States Patent
Wang

(10) Patent No.: US 7,877,341 B2
(45) Date of Patent: Jan. 25, 2011

(54) SELF-ADAPTIVE DATA PRE-FETCH BY ARTIFICIAL NEURON NETWORK

(75) Inventor: Gang Wang, Frederick, MD (US)

(73) Assignee: Microsoft Corporation, Redmond, WA (US)

( * ) Notice: Subject to any disclaimer, the term of this patent is extended or adjusted under 35 U.S.C. 154(b) by 689 days.

(21) Appl. No.: 11/843,642

(22) Filed: Aug. 22, 2007

(65) Prior Publication Data

US 2009/0055333 A1    Feb. 26, 2009

(51) Int. Cl.
    *G06N 5/00*    (2006.01)
(52) U.S. Cl. .......................................... 706/17; 706/45
(58) Field of Classification Search ................... 706/17, 706/45
    See application file for complete search history.

(56) References Cited

U.S. PATENT DOCUMENTS

| | | | |
|---|---|---|---|
| 4,912,651 A | 3/1990 | Wood et al. | |
| 5,255,347 A | 10/1993 | Matsuba et al. | |
| 5,444,619 A | 8/1995 | Hoskins et al. | |
| 6,044,375 A | 3/2000 | Shmueli et al. | |
| 6,466,925 B1 | 10/2002 | Harald et al. | |
| 6,735,580 B1 | 5/2004 | Li et al. | |
| 6,745,169 B1 | 6/2004 | Schlang et al. | |
| 2002/0184569 A1 | 12/2002 | O'Neill | |
| 2006/0155661 A1 | 7/2006 | Morgan | |
| 2006/0230008 A1 | 10/2006 | Burgener | |

OTHER PUBLICATIONS

Yu, et al, Evolving Intelligent Text-Based Agents, Proceedings of the Fourth International Conference on Autonomous Agents, 2000, pp. 388-395.*

Ho Park, et al., "Neural Network Hot Spot Prediction Algorithm for Shared Web Caching System", http://www.springerlink.com/content/tky0930m4y2bxj4g/, Electronics and Information Engineering, Chonbuk National University, Chonju, 561756, South Korea, 12 Pages.

Rangaraja, et al., "Web User Clustering and Its Application to Prefetching Using ART Neural Networks", http://www.selloutwhores.com/~gert/ai/ki2/webuser-clustering-rangarajan.pdf, Department of Computer Science, Department of Electrical Engineering, Louisiana Tech University, 17 Pages.

* cited by examiner

Primary Examiner—Wilbert L Starks, Jr.
(74) Attorney, Agent, or Firm—Turocy & Watson, LLP

(57) ABSTRACT

When a patient enters a medical situation, healthcare professionals can use various amounts of information in evaluating the situation. However, different information can be beneficial dependent on the medical situation. Moreover, personnel can historically use specific information types regardless of the situation. An artificial neuron network is employed to pre-fetch information that personnel likely will want prior to a request from the personnel. In addition, the artificial neuron network can be trained based on results of presented information.

20 Claims, 13 Drawing Sheets

SELF-ADAPTIVE DATA PRE-FETCH BY ARTIFICIAL NEURON NETWORK

TECHNICAL FIELD

The subject specification relates generally to an artificial neuron network and in particular to information pre-fetch using an artificial neuron network.

BACKGROUND

Recently, there have been a large number of advancements in medical science. These advancements relate to new discoveries (e.g., treatment for Poliomyelitis, commonly referred to as polio) as well as to modernization of classical activities (e.g., obtaining a temperature with an electronic thermometer as opposed to a mercury thermometer.) In addition, some individuals can live longer with diseases though different treatment options that can include drugs (e.g., penicillin) and procedures (e.g., dialysis.)

These advancements have lead to development of equipment that can benefit a patient's quality of life. For instance, a person can enter into an emergency room to seek treatment for a heart attack. A nurse can attach an electronic blood pressure monitor to determine internal pressure. In addition, an Electrocardiogram (EKG) can monitor electrical activity of a heart. Results from the EKG and the blood pressure monitor can be used to assess patient condition. Moreover, different tests can be performed on a patient to determine various amounts of medical information. For instance, an X-ray can be used to view an impression of a skeleton.

Medical facilities can range is capabilities, sophistication, resources, etc. There can be large hospitals with attached research facilities and a medical school. However, smaller hospitals with limited resources commonly operate in rural areas. There can also be private practitioners that function out of single offices as well as specialty medical units (e.g., an off-site testing facility.) Various facilities can link together to form partnerships and/or business ventures (e.g., a large city hospital can own several smaller suburban hospitals) to improve patient health. In addition, there can be fringe facilities that practice less accepted medical practices (e.g., herbal remedies) that gain valuable information in patient treatment.

SUMMARY

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as a prelude to the more detailed description that is disclosed later.

The subject specification discloses innovations toward use of an artificial neuron network in providing information to an operator prior to a request from the operator. An artificial neuron network estimates when and what type of information a user would likely desire to appreciate. The information is collected and presented to the user, commonly through a visual display. Feedback information can be obtained that relates to if the user appreciated the information (e.g., the information was beneficial to the user, the information is what the user wanted to see, etc.)

The artificial neuron network can determine errors made in presentations of information and make operational modifications to minimize errors. There can be an expected output of the artificial neuron network as well as an actual output. A comparison between the expected output and actual output can produce a rate of error. The rate of error determines changes that take place to the artificial neuron network.

In addition, a trained artificial neuron network can be transmitted and implemented in multiple systems. This allows new systems to retain functionality of an established system. Moreover, since previous errors by the artificial neuron network have been corrected through training, a new system does not have to re-learn what has been done by a trained artificial neuron network. In addition, the new system can integrate devices that are specific to the system with a trained artificial neuron network (e.g., user profiles.)

The following description and the annexed drawings set forth certain illustrative aspects of the specification. These aspects are indicative, however, of but a few of the various ways in which the principles of the specification can be employed. Other advantages and novel features of the specification will become apparent from the following detailed description of the specification when considered in conjunction with the drawings.

DETAILED DESCRIPTION

Figure 1:
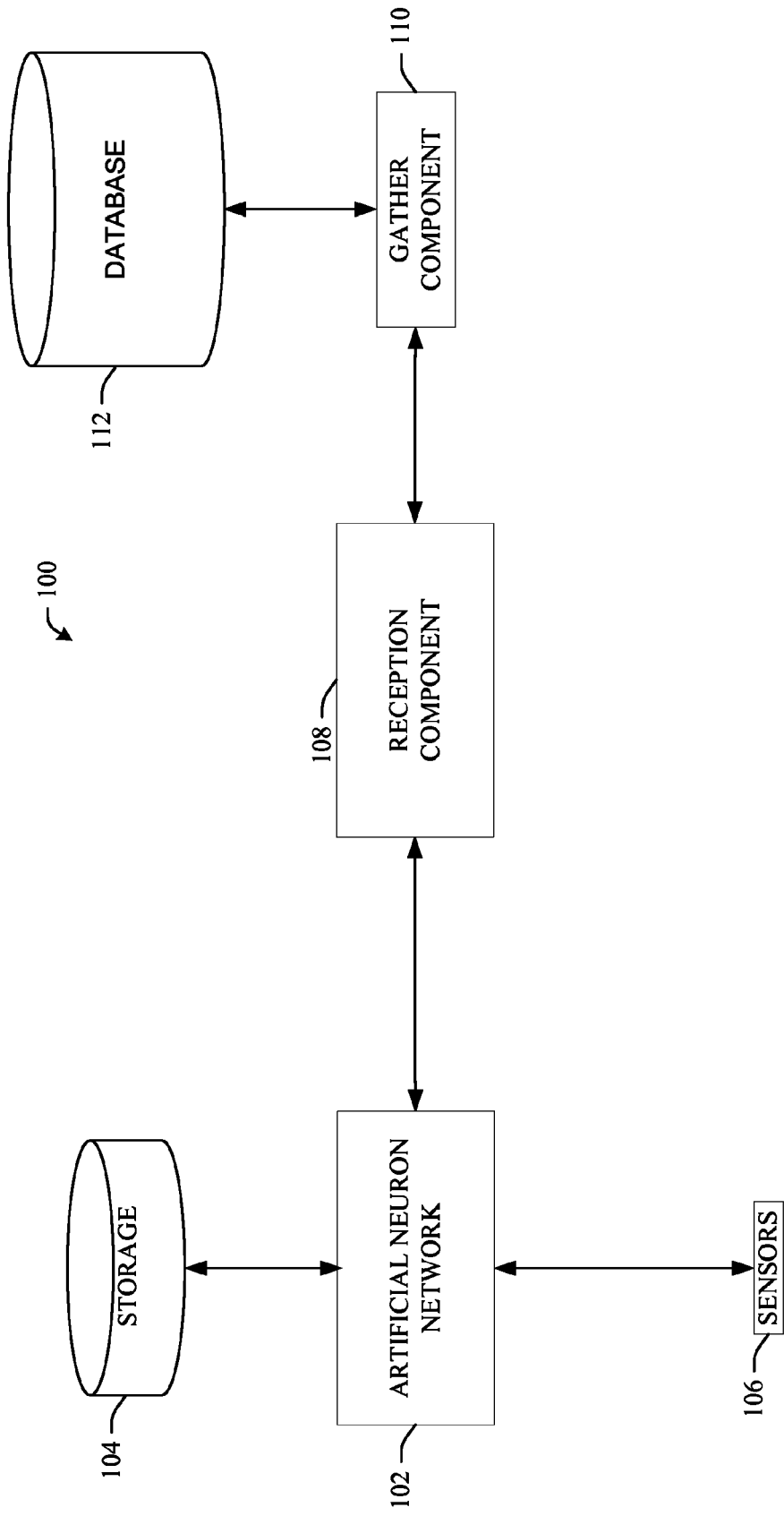
FIG. 1 illustrates a representative system for information pre-fetch in accordance with an aspect of the subject specification.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It can be evident, however, that the claimed subject matter can be practiced without these specific details. In other instances, well-known structures and devices are shown in block diagram form in order to facilitate describing the claimed subject matter.

As used in this application, the terms "component," "module," "system", "interface", or the like are generally intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a controller and the controller can be a component. One or more components can reside within a process and/or thread of execution and a component can be localized on one computer and/or distributed between two or more computers. As another example, an interface can include I/O components as well as associated processor, application, and/or API components.

Furthermore, the claimed subject matter can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications can be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to disclose concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

For purposes of simplicity of explanation, methodologies that can be implemented in accordance with the disclosed subject matter were shown and described as a series of blocks. However, it is to be understood and appreciated that the claimed subject matter is not limited by the order of the blocks, as some blocks can occur in different orders and/or concurrently with other blocks from what is depicted and described herein. Moreover, not all illustrated blocks can be required to implement the methodologies described hereinafter. Additionally, it should be further appreciated that the methodologies disclosed throughout this specification are capable of being stored on an article of manufacture to facilitate transporting and transferring such methodologies to computers. The term article of manufacture, as used, is intended to encompass a computer program accessible from any computer-readable device, carrier, or media.

FIG. 1 discloses an example system 100 for pre-fetching information. An artificial neuron network 102 (e.g., also known as artificial neural network) can gather information from a variety of locations and perform mathematical functions upon the information. An example source of information is storage 104 (e.g., flash memory, random access memory, read-only memory, etc.) Various amounts of information can be held on storage that can be used by the artificial neuron network 102. Previous engagements of different devices can be useful in predicting what data will be useful to a user. In one example, the system 100 can be used in automotive diagnostics. A number of times an automobile was placed in a non-sequential gear can be important in identifying a problem with the automobile. This information is transferred to the artificial neuron network 102.

Storage 104 typically holds at least one piece of profile information used by the artificial neuron network 102 to generate an output. Profile information is at least one detail that relates to a previous experience. Example profiles are an operation profile of a person (e.g., John likes to work with 'Times New Roman' font), manufacture characteristics (e.g., a product's structural support has had a relatively high number of reported failures), etc.

Sensors 106 can be used to obtain information that can be processed by the artificial neuron network 102. Sensors 106 are typically devices that are capable of obtaining contextual data, commonly in real-time. Using an automotive example, sensors can be placed on tires to determine rotations per second. While a plural term sensors 106 is used, it is to be appreciated that the subject specification can be practiced with a single sensor.

In an illustrative operation of the system 100, four pieces of information can enter the artificial neuron network 102 where the pieces are prioritized and analyzed. Functions are performed upon the information and an output (e.g., one or more details) is created. The artificial neuron network 102 creates an output that is at least in part an estimation of information appropriateness for presentment. The output of the artificial neuron network 102 can manifest in a number of different configurations. According to one embodiment, the output can be information pieces with different probabilities of appropriateness (e.g., a visual file has likelihood of 60% while an audio file has likelihood of 45%.) However, the output can be items that pass a certain threshold (e.g., items with a percentage estimation of appropriateness of at least 25%.) For example, if a person reports hearing noise in an engine, then the artificial neuron network 102 can determine that a mechanic likely wants to view engine diagnostic data and not to view data that relates to an air conditioning device.

A reception component 108 obtains at least one output of the artificial neuron network 102. The output can be multiple items with a likelihood (e.g., engine data 85%, air conditioning data >1%), a highest likelihood (e.g., engine data 85%), etc. The reception component 108 can also transmit information to other system components. For example, a confirmation of receipt can be sent to storage 104, where the receipt is saved for diagnostic purposes on the system 100. Moreover, the reception component 108 can emit an output of the artificial neuron network 102 to a gather component 110.

The gather component 110 selects data for presentment based upon received output of the artificial neuron network 102. The artificial neuron network output can be at least in part an estimation of information appropriateness for presentment. It is unlikely the artificial neuron network 102 works with actual files; the artificial neuron network 102 likely works with representations. The gather component 110 can select data based on a representation associated with the output. According to one embodiment, the artificial neuron network 102 does work with files and selection includes accepting an output of the artificial neuron network 102, extracting data, etc. Data selected by the gather component 110 is commonly fetched or presented prior to a request for the data. This increases efficiency since a user does not need to make a request; the system 100 intelligently provides the user with information that has a relatively high likelihood of being appropriate (e.g., useful.)

Commonly the data is selected from a database 112. A database 112 can be used to hold a relatively large amount of information. The database 112 can be a single location or be distributed over multiple locations. Moreover, the storage 104 and database 112 can integrate together to form a single location. According to another embodiment, data is retrieved from a remote location through utilization of a communication component (e.g., download from an off-site server.)

Output of the artificial neuron network 102 can relate at least in part to a creature condition. A creature condition is a status of a creature. A creature can include a human, mammal, animal, plant, fungus, bacteria, etc. Commonly, the status relates to the health of the creature, such as their medical history, current medical condition, etc. While often a physical condition, a creature condition can include psychological condition, spiritual condition, etc. For instance, the output of the artificial neuron network 102 can be a disclosure of a person's religious affiliation. The person could be dying and a visit from a spiritual leader of the religious affiliation can improve the person's quality of life and/or short-term health. Since quality of life can be a creature condition, then the religious affiliation relates to the creature condition.

The following is an illustrative example of an implementation of the system 100 in accordance with an aspect of the subject specification. A patient can enter an emergency room after suffering a heart attack. It is possible that a person can die from a heart attack if not treated properly and quickly; with a heart attack time can become important (e.g., receiving quick treatment.) Storage 104 can transfer various amounts of information to the artificial neuron network 102. For instance, a particular doctor, 'Doctor_A', can be on duty in the emergency room. Storage 104 can hold a profile for Doctor_A that discloses pervious tendencies. An example tendency is Doctor_A typically does not care about information concerning patient appendages and Doctor_A concentrates on core information (e.g., information that relates to vital organs.) This information can transfer to the artificial neuron network 102.

In addition, patient information can be obtained through the sensors 106. Sensors can encompass a wide variety of devices. An Electrocardiogram (EKG) can gather information that relates to a patients heart rate through placement of pads on a patient's chest. In addition, an X-ray can be taken of a patient's chest cavity and be transferred to the artificial neuron network. Further processing can take place of sensed information. For instance, an X-ray can be taken by the sensors, developed, and then saved in storage 104. The storage 104 transfers at least on detail relating to a developed X-ray to the artificial neuron network 102.

The artificial neuron network 102 creates an output that is at least in part an estimation of information appropriateness for presentment. A relatively large amount of information can enter the artificial neuron network 102, including a patient's medical history from a number of different hospitals/care centers (e.g., doctor's office.) If a patient is receiving treatment for a heart attack, then it is unlikely Doctor_A desires to view the patient's treatment for acne forty years ago. The artificial neuron network 102 estimates information that Doctor_A will likely want to see. This commonly takes place prior to a request from Doctor_A to see information. An example piece of information is a chest X-ray taken recently and this information is outputted.

The artificial neuron network 102 transfers the X-ray information to the reception component 108. The reception component 108 transfers the X-ray information to the gather component 110. The gather component 110 access an actual X-ray referred to by the information from the database 112.

Innovation disclosed in the subject specification goes against conventional wisdom. Using a medical example, information can be a difference between life and death for a patient. Therefore, it would appear illogical to estimate information for presentation due to severity of related consequences (e.g., wrong information can cost a person their life.) However, use of an artificial neuron network 102 can produce accurate results such that estimating information can be overall safer since medical personnel can focus more attention on a patient and not have to make conscious requests. Thus, estimation of information appropriateness can become more beneficial since error rates can be relatively low and time does not have to be dedicated to making a request if correct information is pre-fetched; even if information is incorrectly pre-fetched, an operator makes a request which is no more of a burden then what takes place in conventional systems.

Figure 2:
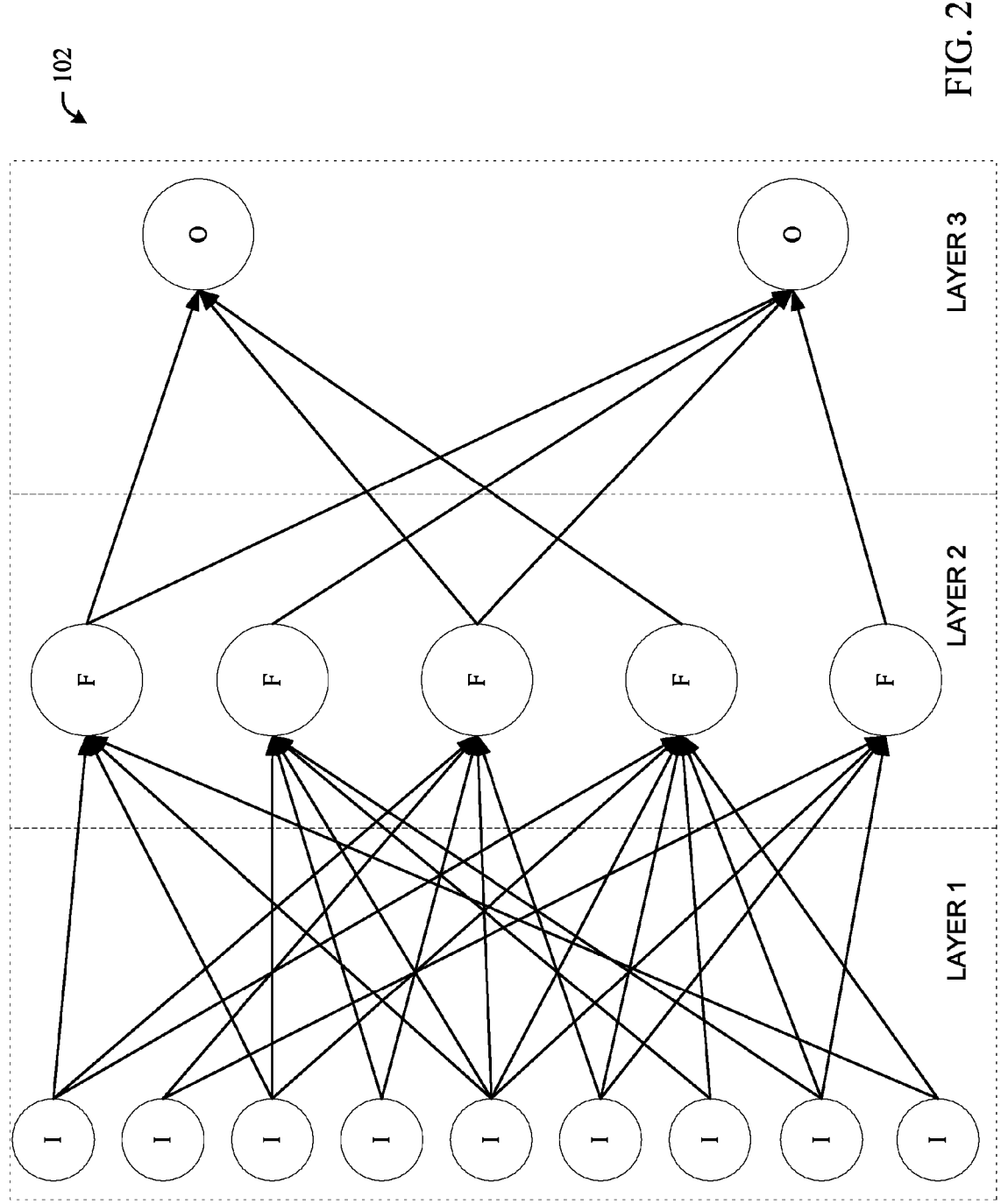
FIG. 2 illustrates a representative artificial neuron network in accordance with an aspect of the subject specification.

FIG. 2 discloses an example artificial neuron network 102. The artificial neuron network can have three layers, signified as layer 1, layer 2, and layer 3. A layer commonly includes at least one neuron that processes information. Neurons in different layers can connect with one another through paths. A common artificial neuron network 102 is a non-linear statistical data-modeling tool.

In the disclosed artificial neuron network 102, layer 1 includes nine input neurons I. Various operations can occur upon the input neurons I to determine where results of the input neurons I should travel. Results can move to one or more function neurons F disclosed through various paths. Layer 2 embraces five function neurons F that perform at least one process (e.g., mathematical operation) upon results of the input neurons. Processed results can travel to two output neurons 0 located as part of layer 3. The output neurons 0 can disclose an output that is obtained by the receiving component 108 of FIG. 1.

In one configuration, the artificial neuron network 102 is a three-layer feed-forward artificial neuron network 102, which can be a multi-layer perception. A three-layer artificial neuron network allows individual neurons to be placed into three distinct groups. A feed-forward artificial neuron network allows neurons to connect without forming a complete cycle (e.g., neurons in one layer connect with neurons in a subsequent layer.)

Figure 3:
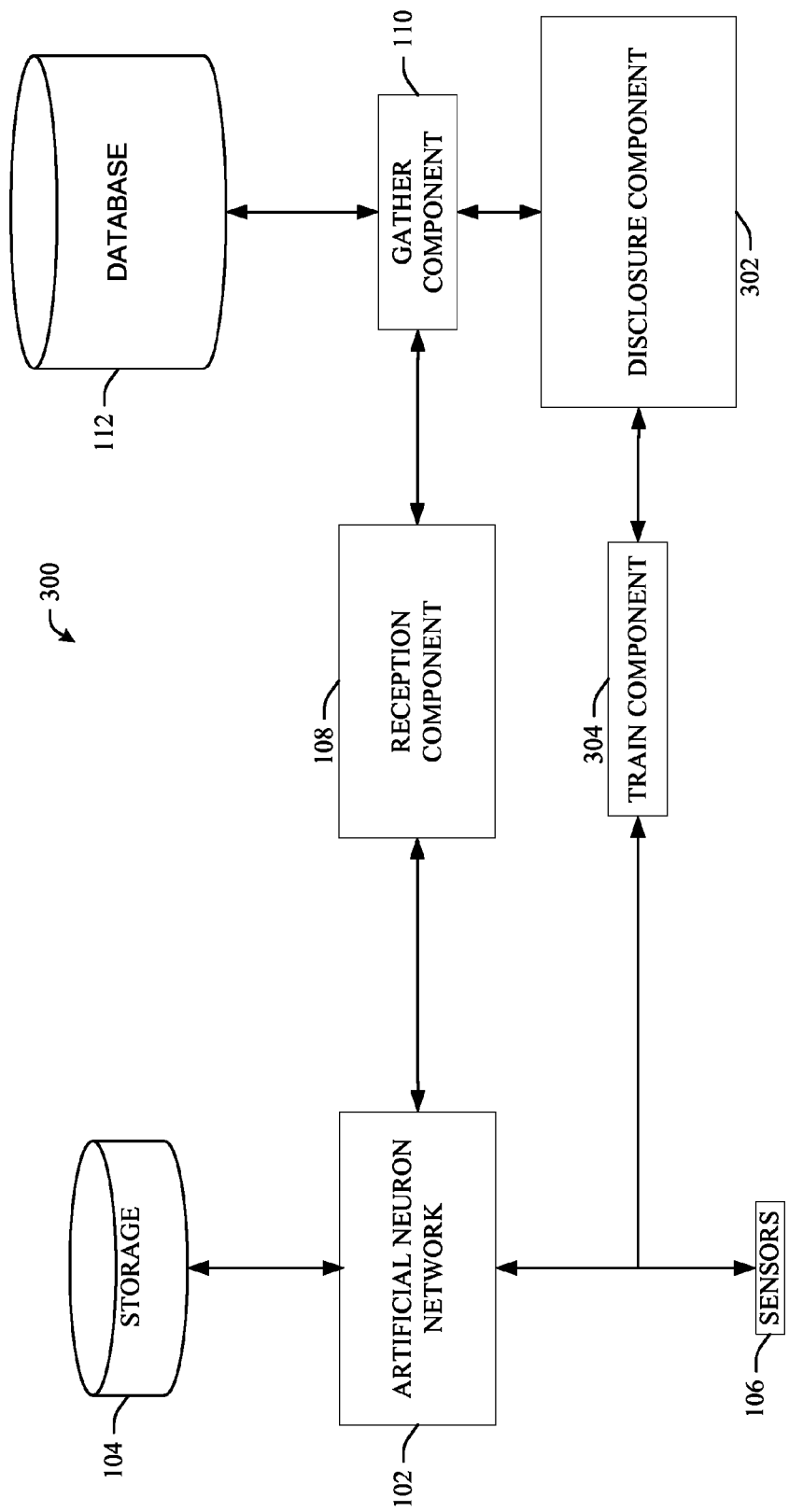
FIG. 3 illustrates a representative system for information pre-fetch with artificial neuron network alteration with presentation capabilities in accordance with an aspect of the subject specification.

FIG. 3 discloses an example system 300 with a disclosure component 302 and a train component 304. An artificial neuron network 102 receives information from storage 104, sensors 106, etc. Based on received information, the artificial neuron network 102 creates an output that is at least in part an estimation of information appropriateness for presentment. The output travels to a reception component 108 that obtains output of the artificial neuron network 102. A gather component 110 selects data for presentment based upon output of an artificial neuron network 102. The gather component 110 can transfer selected data to the disclosure component 302.

The disclosure component 302 presents data selected by the gather component 110. Data selected by the gather component 112 can take a number of different forms. The gather component 110 can obtain a visual file that discloses a picture. The disclosure component 302 can determine a detail level of the picture and choose a resolution to disclose the picture properly.

In order to make an appropriate choice, the disclosure component 302 can include a processor and internal logic (e.g., artificial intelligence.) For instance, the picture can be of an infrared image of a collapsed building where people are trapped inside. A higher resolution image can be more beneficial, so the disclosure component 302 can determine that presenting data at a higher resolution would be beneficial and thus present the image at a determined resolution level. The disclosure component 302 can encompass a number of different configurations, including a monitor, printer, speaker system, etc.

In addition, the disclosure component 302 can include a modification component that alters data obtained by the gather component 110. Information collected by the gather component 110 can be relatively detailed and include detail that surpasses capability of the disclosure component 302. In one illustrative example, data obtained is in color while the disclosure component 302 presents images without color (e.g., black-and-white, grayscale, etc.) The modification component 302 changes data from color to without color and presents the data. Moreover, if presentation of high detail information would be time consuming while the information is important to be presented quickly, then the disclosure component can present the information in a low quality state.

Moreover, the disclosure component 302 can utilize other units disclosed in the system 300. For example, the disclosure component 302 can be a monitor integrated with a speaker. A person using the system can be blind, therefore making a visual presentment relatively unbeneficial. While the artificial neuron network 102 can take the person's lack of sight into account, an output can still disclose that text is appropriate for presentment. The gather component 110 can obtain text from the database 112 and transfer the text to the disclosure component 302. The disclosure component 302 can access a profile in storage 104 and determine a visual display would not be beneficial. Therefore, the disclosure component 302 modifies the text to an audio file (e.g., through a text-to-speech application) and presents the text as sound so it can be appreciated by the person.

The train component 304 modifies the artificial neuron network 102 based off at least one output of the artificial neuron network 102. The disclosure component 302 can reveal information to a user and the user can ignore the information (e.g., user response). A user ignoring information can be a sign that presented information was not beneficial and thus output of the artificial neuron network 102 was not beneficial. Based on a reaction to the output, the train component 304 modifies operation of the artificial neuron network 102. In one configuration, modification of the artificial neuron network 102 based off at least one output of the artificial neuron network 102 includes strengthening a position (e.g., re-affirming that operation is correct, making it more difficult to undo a portion, etc.)

The train component 304 can communicate with the disclosure component 302 and obtain active feedback from a user. For instance, the disclosure component 302 can present a questionnaire to a user asking if the presented information was helpful, if it was what the user desired, etc. Depending on a response, the train component 304 can modify the artificial neuron network 102. A response to an output (e.g., through presented information) to base a modification off of can be obtained through an active manner (e.g., questionnaire), passive manner (e.g., time between presentation of information and when information is closed, determining if data was obtained by the user in a non-pre-fetch manner, etc.), etc.

Moreover, the train component 304 can determine a rate of error that relates to operation of the artificial neuron network 102. Prior to operation of the artificial neuron network, the train component 304 can use an estimation component to predict a likely output. The train component compares an estimated output against an actual output. A rate of error is calculated and analyzed; based on calculation and analysis, the train component 304 makes a modification upon the artificial neuron network 102.

According to another embodiment, the train component 304 holds instructions that are incorporated into the artificial neuron network 102. A developer can connect to the train component through a terminal and present instructions to the artificial neuron network 102 with data describing factors that can influence pre-fetch efficiency. In a medical context, example factors can include: when a patient checked into a hospital and whether the patient is already discharged, which department was a patient admitted to (e.g., emergency room patient in general is more time critical than walk-in clinic), patient symptom, is a current user the physician or nurse in charge of the patient, when was the last time that the current user requested information of the patient, what type of information did the current use request previously for the patient or for another patient, etc. Importance of factors can transfer to an artificial neuron network 102 and the factors are used to modify operation.

Figure 4:
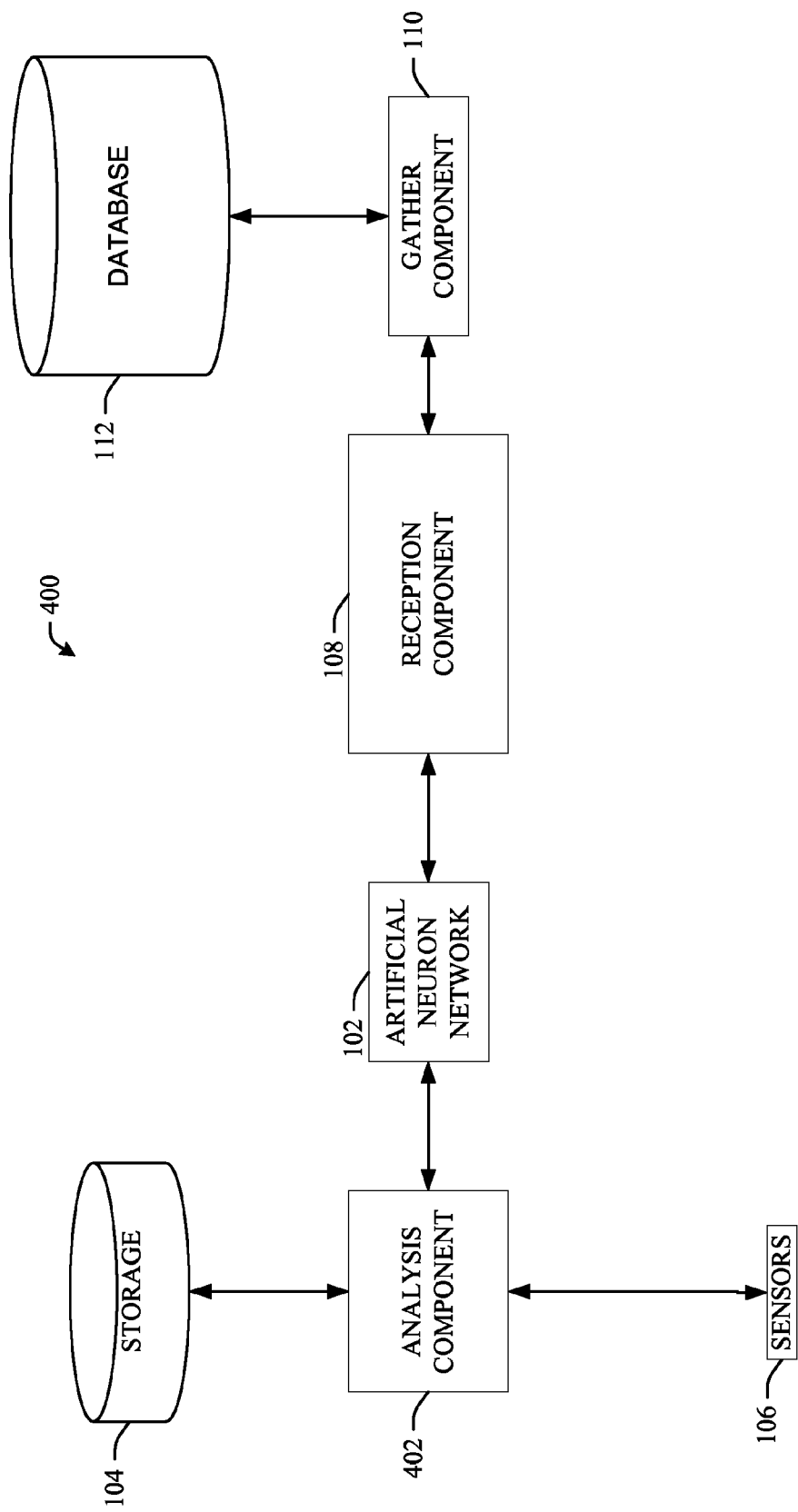
FIG. 4 illustrates a representative information pre-fetch system with an analysis component in accordance with an aspect of the subject specification.

FIG. 4 discloses a system 400 for producing information that is estimated to be beneficial to an individual through use of an analysis component 402. Storage 104, sensors 106, etc. can send information that can be used by an artificial neuron network 102 to an analysis component 402. The analysis component 402 can perform a number of evaluations related to information (e.g., about one or more evaluations.) For instance, it is possible that the artificial neuron network 102 becomes flooded with information; there is so much information that performance is hindered (e.g., operation takes too long, crash, etc.) The analysis component 402 can selectively emit information to the artificial neuron network 102.

In addition, the analysis component 402 can retain statistics that relate to information passing to the artificial neuron network 102. For instance, a large amount of information can be coming from a particular group of sensors (e.g., a group of heart sensors are used frequently in an operation room when a particular doctor is operating.) The analysis component 402 can make a note of a tendency and transmit the note to a train component 304 of FIG. 3. The train component 304 of FIG. 3 can make an inference (e.g., thorough artificial intelligence.) that a doctor would find information from heart sensors more appropriate since a relatively large amount of information is produced from heart sensors. Based on the evaluation of the analysis component 402, the train component 304 of FIG. 3 makes a modification of the artificial neuron network 102.

An artificial neuron network 102 obtains information from the analysis component 402. Based on obtained information, the artificial neuron network 102 can generate an output that is at least in part an estimation of how appropriate information is for presentment. The analysis component 402 evaluates at least one piece of information used by the artificial neuron network to create an output. The output transfers to a reception component 108 that collects output of the artificial neuron network 102. A gather component 110 chooses data for presentment based upon output of an artificial neuron network 102.

Figure 5:
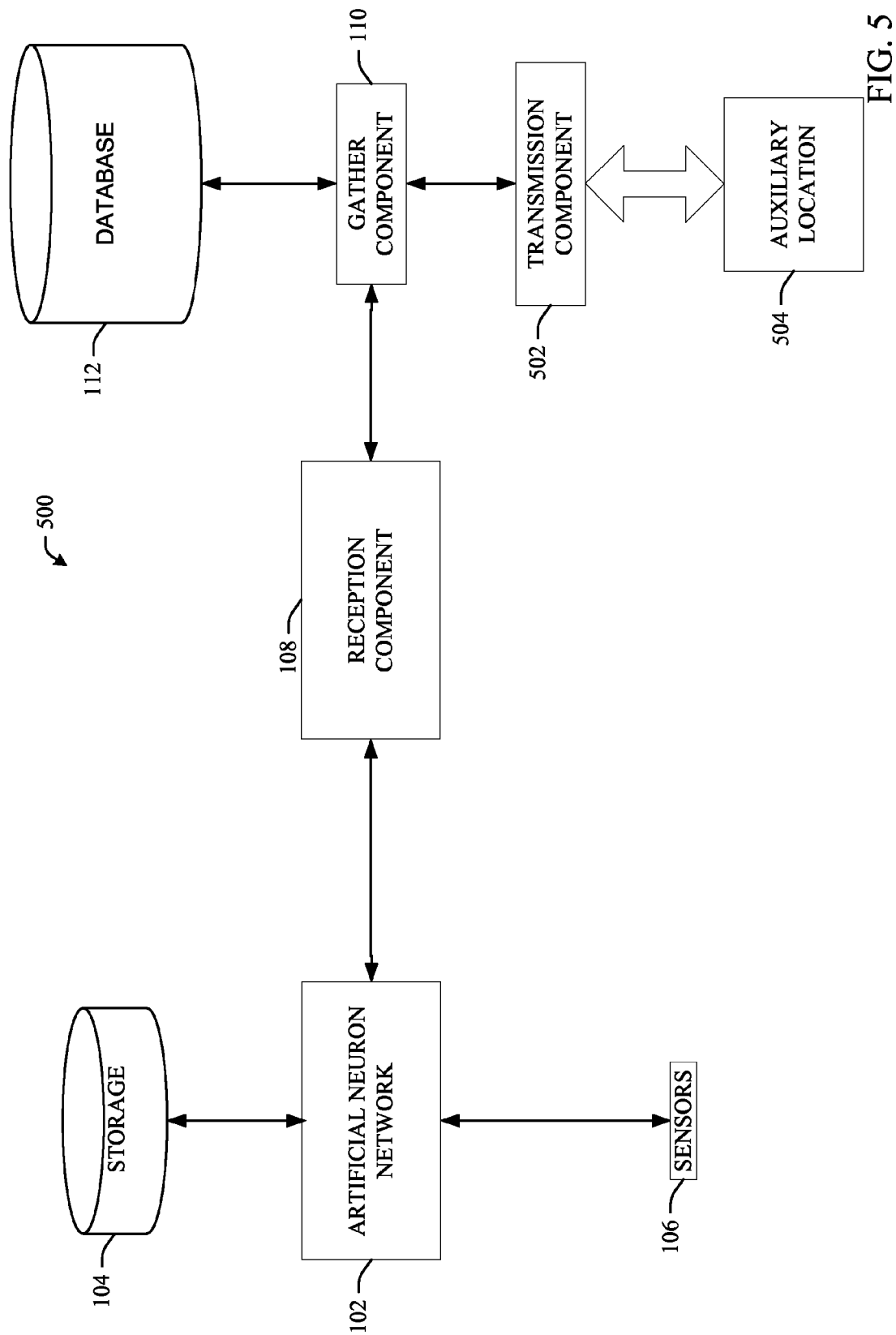
FIG. 5 illustrates a representative system for transferring an artificial neuron network to another location in accordance with an aspect of the subject specification.

FIG. 5 discloses a system 500 for information pre-fetch that uses a transmission component 502 to communicate with an auxiliary location 504. An artificial neuron network 102 obtains information from storage 104, sensors 106, etc. Based on obtained information, the artificial neuron network 102 can generate an output that is at least in part an estimation of information appropriateness for presentment. The output transfers to a reception component 108 that collects output of the artificial neuron network 102. A gather component 110 chooses data for presentment based upon output of an artificial neuron network 102.

Another system can be created that can benefit from use of an artificial neuron network 102 that has had a level of training (e.g., been trained at least once.) The transmission component 502 can emit the artificial neuron network 102 (e.g., a copy of the artificial neuron network 102) to an auxiliary location 504. The transmission component 502 can include a signal component that obtains a message that the artificial neuron network 102 is to be transferred to an intended location. Verification can take place to determine if the intended location is authorized to receive the artificial neuron network 102. An encode component of the transmission component 502 can encrypt the artificial neuron network 102 to increase security. Once transfer of the artificial neuron network 102 is complete, a reception message can be received through the signal component.

Figure 6:
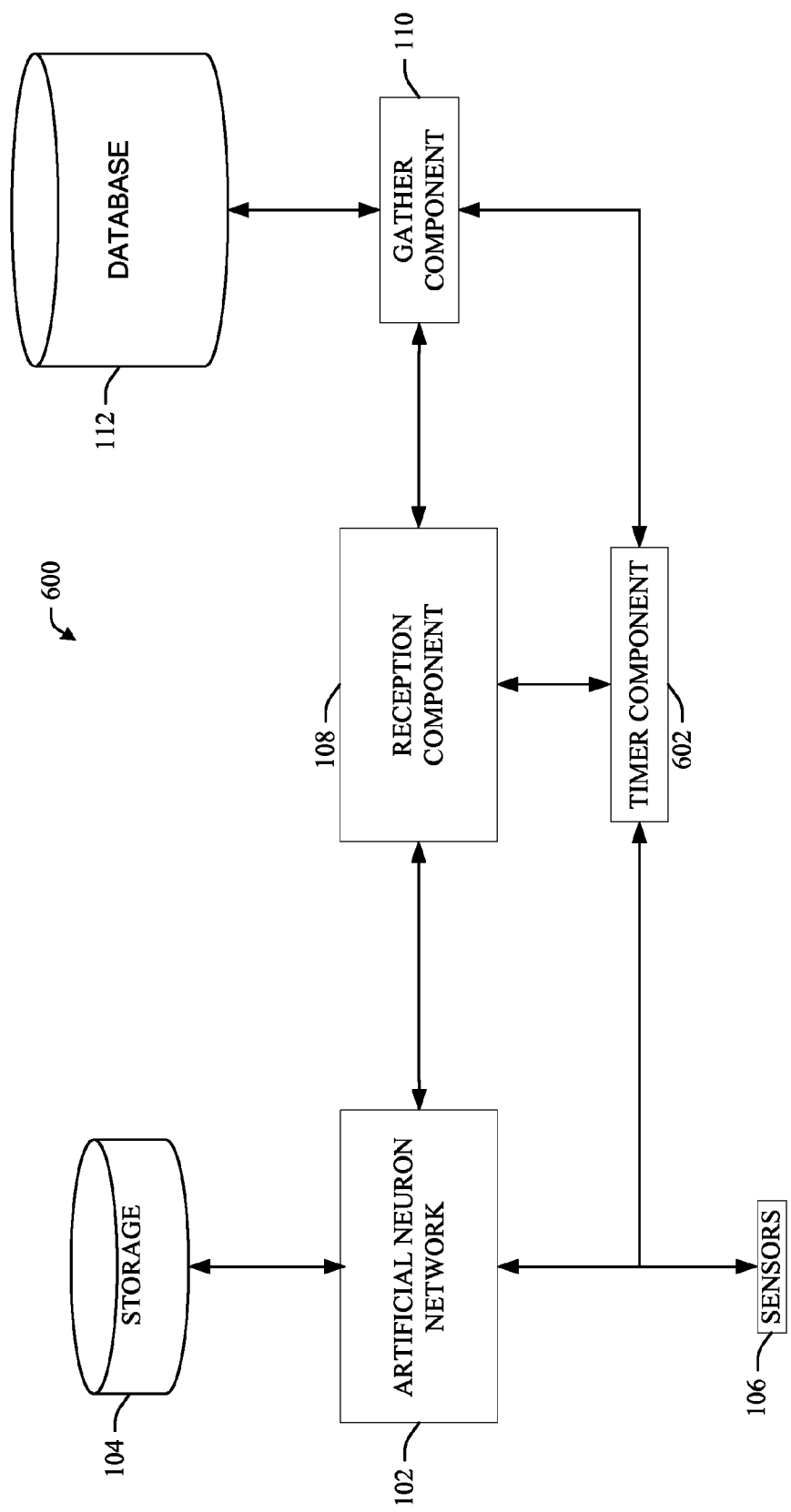
FIG. 6 illustrates a representative system for information pre-fetch with a timer component in accordance with an aspect of the subject specification.

FIG. 6 discloses an example information pre-fetch system with integration of a timer component 602. An artificial neuron network 102 attains information from storage 104, sensors 106, etc. Based on attained information, the artificial neuron network 102 can produce a yield that is at least in part an assessment of information appropriateness for presentment. The yield transfers to a reception component 108 that collects yield of the artificial neuron network 102. A gather component 110 chooses data for presentment based upon yield of an artificial neuron network 102.

The system 600 can operate with a time constraint that is managed by the timer component 602. For instance, if the system 600 operates in a medical scenario, then it can become important that information is produced quickly. Therefore, the timer component 602 can regulate operation of the system 600 to assure that operates are completed (e.g., that ultimately information is presented) in a desired amount of time.

The timer component 602 determines when presentment of selected data is beneficial. While disclosed as an independent component, it is to be appreciated that the artificial neuron network 102 can implement the timer component 602. A prediction includes reading an instructed amount of time. For example, a timer component can have an instruction that data is to be presented within about 0.0125 seconds. This is still a prediction since it is not known that this will be beneficial.

The timer component 602 can evaluate when a user actually desires information. A comparison can be made between when the artificial neuron network 102 predicted information to be beneficial and when it is actually beneficial. A result of the comparison can be used by the train component 304 of FIG. 3 to alter operation of the artificial neuron network 102. If actual time is before predicted time, then the artificial neuron network 102 can be trained to hasten operation; if predicted time is before actual time, then the artificial neuron network 102 can be trained to take more time to perform more through evaluations. According to one embodiment, the timer component 602 sends a signal to the artificial neuron network 102 with an amount of time to complete operation. The timer component 602 can include a clock component that measures how long an operation takes and/or measures an actual time. Determination of when presentment of selected data is beneficial includes prediction as well as timing.

Figure 7:
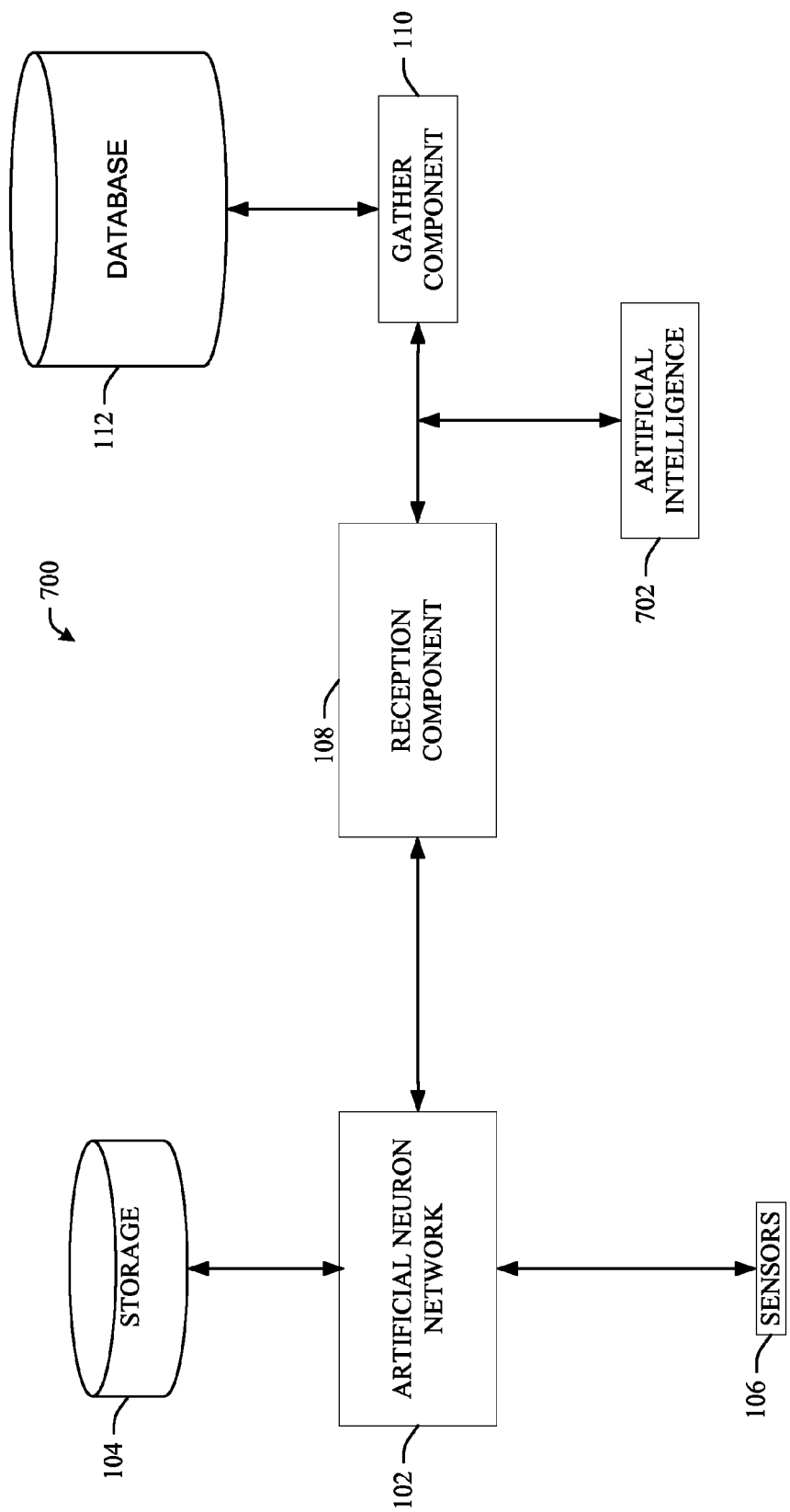
FIG. 7 illustrates a representative data pre-fetch system implementing artificial intelligence in accordance with an aspect of the subject specification.

FIG. 7 discloses an example information pre-fetch system 700 utilizing artificial intelligence 702. An artificial neuron network 102 obtains information from storage 104, sensors 106, etc. Based on obtained information, the artificial neuron network 102 can generate an output that is at least in part an estimation of information appropriateness for presentment. The output transfers to a reception component 108 that collects output of the artificial neuron network 102. A gather component 110 chooses data for presentment based upon output of an artificial neuron network 102.

Artificial intelligence 702 makes at least one inference or at least one determination or at least one of each in relation to selection of data. Various scenarios can occur that are processed by the artificial intelligence 702. For example, the artificial intelligence 702 can identify that a patent has entered an emergency room. A determination can be made that an output of medical records should be made and the artificial intelligence 702 sends a signal to the artificial neuron network 102 to commence operation. The artificial intelligence 702 can also be adaptive (e.g., in a manner similar to adaptation of the artificial neuron network.) and thus change as conditions are learned that related to operation of the system 100.

Artificial intelligence 702 can employ one of numerous methodologies for learning from data and then drawing inferences and/or creating making determinations related to data selection (e.g., Hidden Markov Models (HMMs) and related prototypical dependency models, more general probabilistic graphical models, such as Bayesian networks, e.g., created by structure search using a Bayesian model score or approximation, linear classifiers, such as support vector machines (SVMs), non-linear classifiers, such as methods referred to as "neural network" methodologies, fuzzy logic methodologies, and other approaches that perform data fusion, etc.) in accordance with implementing various automated aspects described herein. Methods also include methods for the capture of logical relationships such as theorem provers or more heuristic rule-based expert systems. Various components of the system 700 can utilize the artificial intelligence 702 in operation. For instance, the disclosure component 302 of FIG. 3 can use artificial intelligence 702 to determine a detail level for presentation of information.

Figure 8:
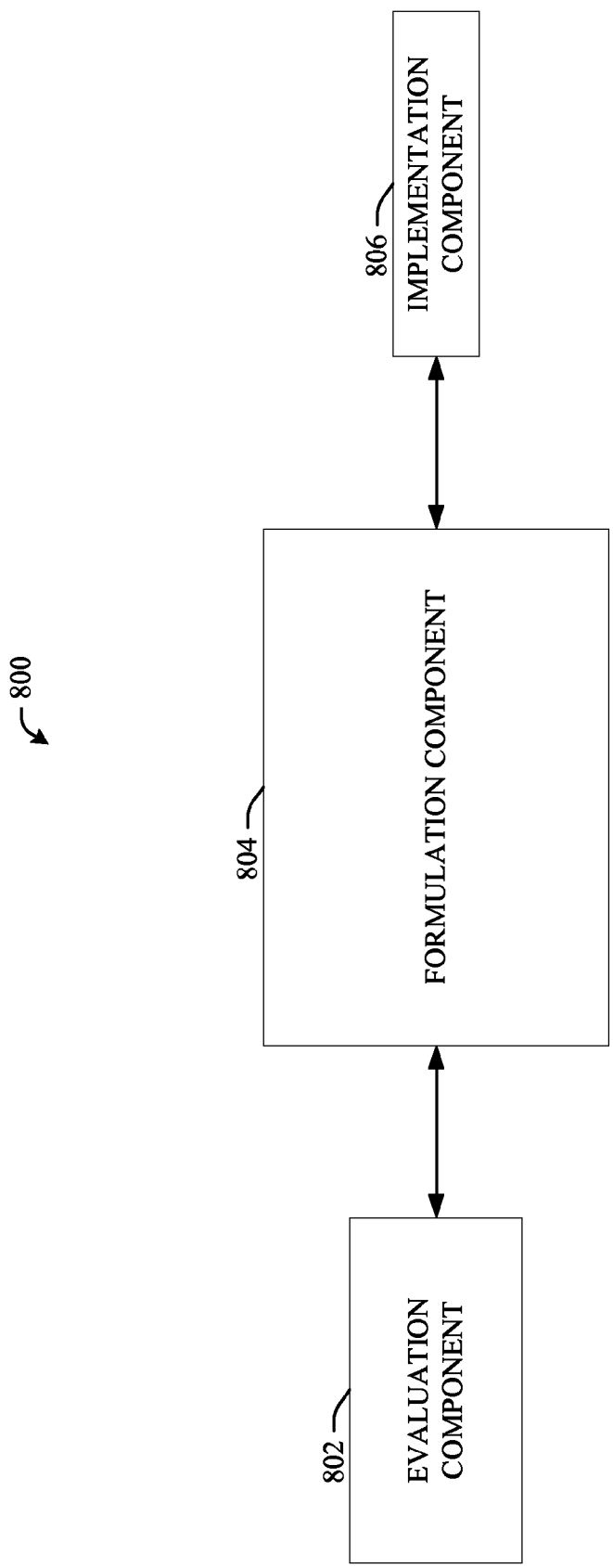
FIG. 8 illustrates a representative data pre-fetch strategy system in accordance with an aspect of the subject specification.

FIG. 8 discloses an example strategy implementation system 800 for use in conjunction with an artificial neuron network 102 of FIG. 1. Various factors can be taken into account by an artificial neuron network 102 of FIG. 1. In order to function efficiently, an approach can be developed for operation of the artificial neuron network 102 of FIG. 1.

An evaluation component 802 can determine context of various factors to be considered by the artificial neuron network 102 of FIG. 1. For instance, two factors can be used for a medical execution of the system 800. A first factor is if a patient is breathing and a second factor is if a patient is a vegan. If the system 800 is placed in an emergency room, then the evaluation component 802 can determine that the first factor is highly important while the second factor is not important. In contrast, if the system 800 is used in a hospital kitchen, the second factor can be more important than the first factor. The evaluation component 802 can function as a means for evaluating at least one factor that impacts information pre-fetch A formulation component 804 creates a strategy that is to be used by the artificial neuron network 102 of FIG. 1. The strategy is based off output of the evaluation component 802. For instance, the evaluation component 802 can send a message to the formulation component 804 disclosing that a first factor and a second factor are present and that the system 800 is located in an emergency room. Based on the received information, a plan of operation for the artificial neuron network 102 of FIG. 1 is developed.

An implementation component 806 practices a strategy created by the formulation component 804. According to one embodiment, the implementation component 806 is the artificial neuron network 102 of FIG. 1. The implementation component 806 can manifest in other configurations, such as sending a signal to the artificial neuron network 102 of FIG. 1 that allows the artificial neuron network 102 of FIG. 1 to follow the strategy. The implementation component 806 can practice as a means for implementing the strategy.

Figure 9:
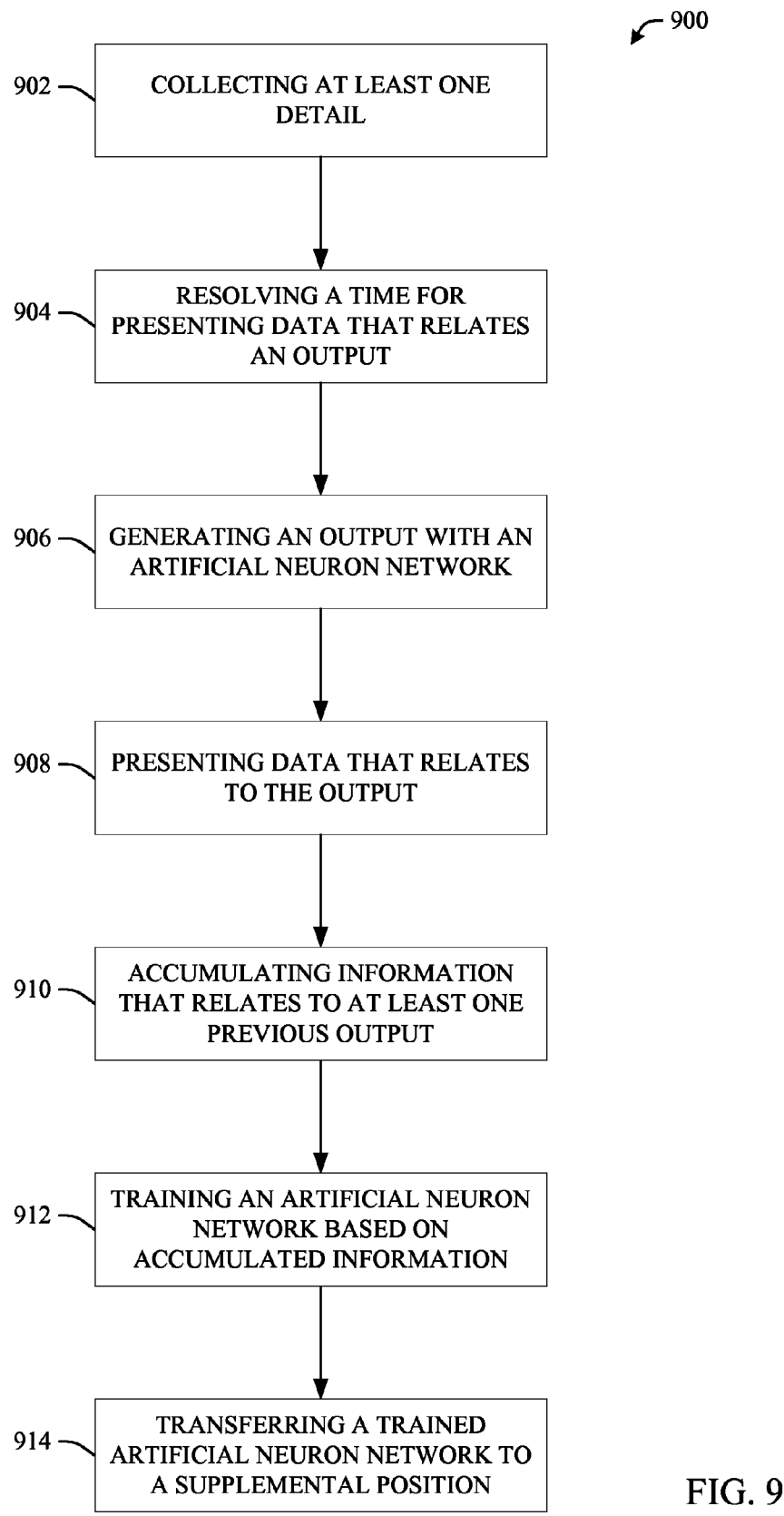
FIG. 9 illustrates a representative artificial neuron network training methodology in accordance with an aspect of the subject specification.

FIG. 9 discloses an example methodology 900 for training an artificial neuron network. Action 902 is collecting at least one detail. Various details can become important on disclosing information that is to be presented, commonly prior to a request of the information. Details can include contextual information that an artificial neuron network can use in generating an output There is resolving a time for presenting information that relates to an output 904. There can be time constraints related to presenting information. For example, information can be of high importance and/or a system operating the methodology 900 can have a goal time that is to be met (e.g., about 0.0125 seconds.) Action 904 allows an artificial neuron network to operate within projected time constraint. In addition, other units in a system operating the methodology 900 can be aware of how quickly to operate.

Event 906 is generating an output with an artificial neuron network. An output commonly provides instruction as to what information is to be presented. However, the methodology 900 can configure to allow the output to be what is ultimately presented. Generation can take place in accordance with manners disclosed in the subject specification. Presenting data that relates to the output 908 occurs. Presentation of data allows a user to appreciate the data and to act upon the data. Typically, data is presented prior to a request from a user.

Accumulating information that relates to at least one previous output 910 can take place. Various reactions can take place in accordance with an output. For instance, a user can have a level of satisfaction regarding presented data that relates to an output. Presented data can be what a user desires, can be beneficial to the user, can be helpful yet not what the user would have highly desired, be partially what a user desired, but not beneficial, etc. The level of satisfaction is accumulated in event 910 through passive observance, active observation, etc.

There is training an artificial neuron network based on accumulated information 912, commonly done in whole or in part. Training allows an artificial neuron network to operate in a more accurate manner, produce higher quality information, determine an improved artificial neuron network structure, etc. According to one embodiment, modification of operational structure of the artificial neuron network occurs (e.g., changing mathematical equations used as part of operation of the artificial neuron network.) Training typically takes place automatically (e.g., without interaction from a developer.) Training an artificial neuron network goes against general rationale. Since the methodology 900 can be practice in areas where errors become important (e.g., medical situations), it can be viewed as irrational to alter what a person has created with an automatic modification. However, automatic training can produce more beneficial results since an artificial neuron network can be up-to-date and is typically able to appreciate greater information than a developer writing code. In addition, it can be cumbersome for a person to write code for small modifications that can improve operation, so automatic training allows for efficient changes and possibly less down time (e.g., in a scenario where a system operating the methodology 900 is taken offline to make a modification.)

Act 914 is transferring a trained artificial neuron network to a supplemental location. A signal can be received from the supplemental location requesting the trained artificial neuron network. Verification can take place to assure that the supplemental location is authorized to receive the artificial neuron network. A transfer occurs and once the artificial neuron network is successfully transmitted, it can be installed at a new location (e.g., the supplemental location, a third location that receives the artificial neuron network from the supplemental location, etc.)

Figure 10:
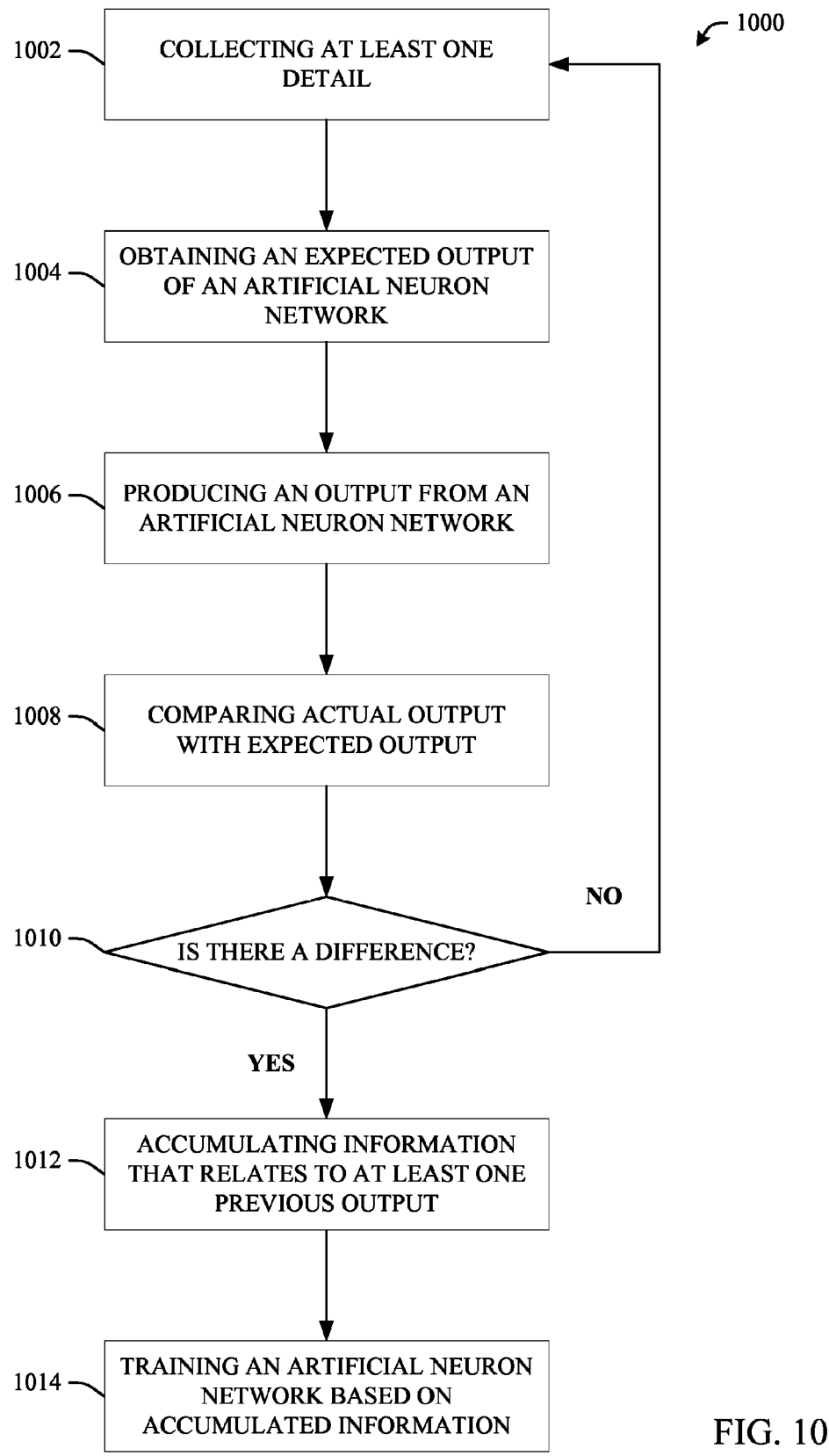
FIG. 10 illustrates a representative error determination methodology in accordance with an aspect of the subject specification.

FIG. 10 discloses an example methodology 1000 for calculation of a rate of error and using the rate of error to train an artificial neuron network. Action 1002 is collecting at least one detail. Details can become significant concerning presentation of information to a user. Details encompass contextual records that an artificial neuron network can apply in generating an output. An example detail is a time of day information will be presented.

There is obtaining an expected output of an artificial neuron network 1004. Based on collected details, estimation can take place as to what an output should be used to base information to be presented. This can take place according to a number of different embodiments. For instance, a look-up table can be utilized where information relates to a value. If one detail is collected related to time of day, then an output of '1' can be expected for daytime and an output of '0' if a detail is nighttime.

Generating an output from an artificial neuron network 1006 occurs. An output commonly provides instruction as to what information is to be presented. However, the methodology 1000 can configure to allow the output to be what is ultimately presented. Generation can take place in accordance with manners disclosed in the subject specification. Presenting data that relates to the output 1006 occurs. Presentation of data allows a user to appreciate the data. Typically, data is presented prior to a request from a user.

Event 1008 is comparing an actual output with expected output. Comparing determines similarities and/or differences between the outputs. A check 1010 takes place to determine a difference between an actual output and expected output. If there is no difference, then the methodology 1000 can continue which can include a return to event 1002. If there is a difference (e.g., a substantial difference, even a small difference, etc.), then the methodology 100 continues to action 1012.

Accumulating information that relates to at least one previous output (e.g., expected output, actual output, etc.) 1012 can take place. A result of event 1008 can become accumulated information. Various reactions can take place in accordance with an output. For instance, a user can be presented with questions that relates to quality and relevance of presented information. The user can respond to the questions and answers of the questions are accumulated by event 1012.

There is training an artificial neuron network based on accumulated information 1014. Artificial neuron network training can be based on accumulated information alone or in part based on accumulated information. Training allows an artificial neuron network to operate in a more efficient manner, produce higher quality information, operate in a quicker manner, etc. According to one embodiment, alteration of an operational structure of the artificial neuron network occurs (e.g., altering a number of neurons in different layers that are used by the artificial neuron network.)

Figure 11:
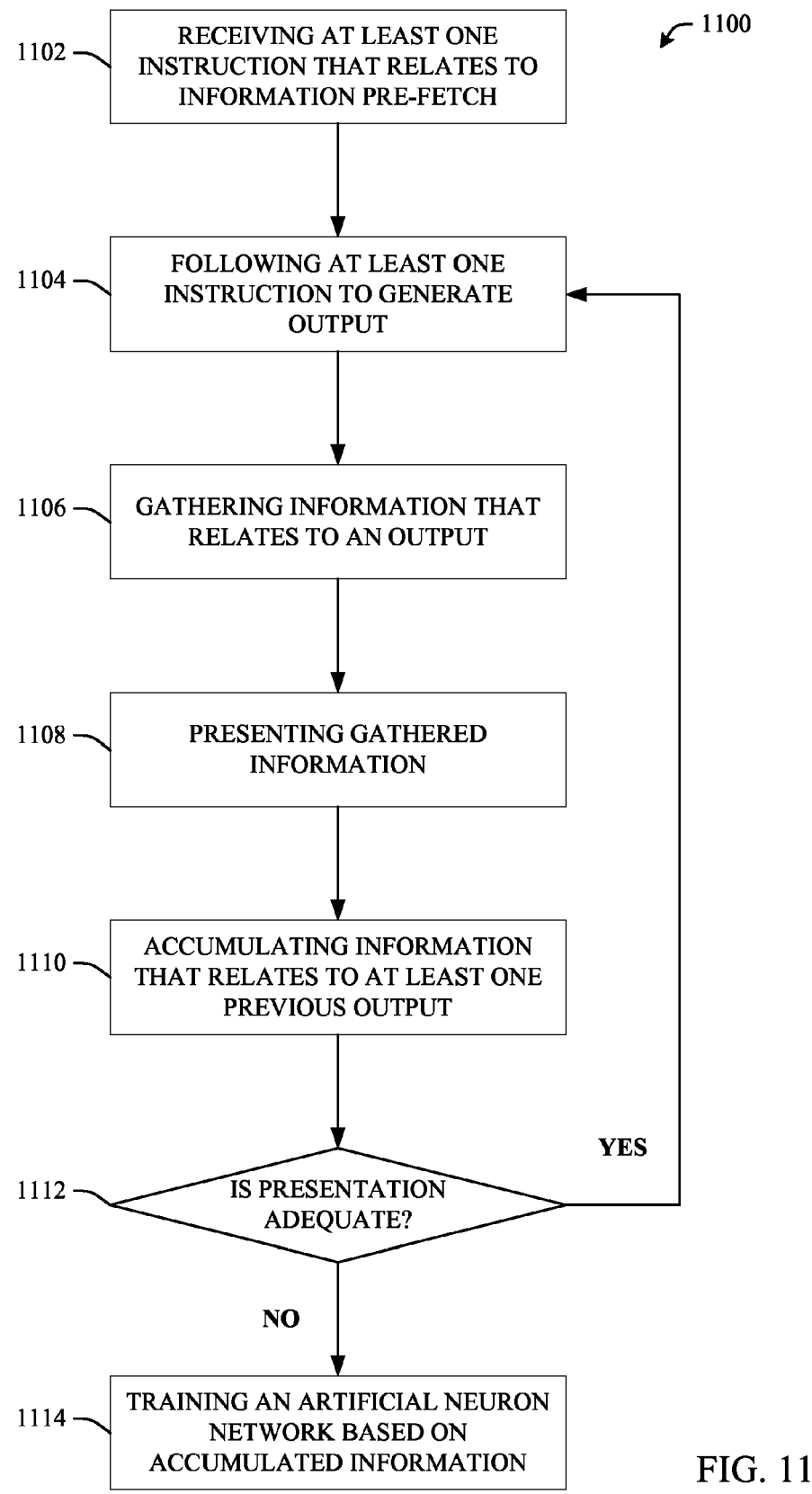
FIG. 11 illustrates a representative feedback methodology in accordance with an aspect of the subject specification.

FIG. 11 discloses an example methodology 1100 for instruction coordination with an artificial neuron network. There is receiving at least one instruction that relates to information pre-fetch at event 1102. Commonly, a programmer lists several instructions (e.g., factors) that an artificial neuron network is to consider when generating an output. These instructions are received so they can be utilized by the artificial neuron network. Received instructions can be configured into a strategy, in an unorganized manner, etc.

Following at least one instruction to generate output 1104 (e.g., generate output for a visual display) occurs. If a strategy is provided, then the instructions can be following in accordance with the strategy (e.g., a strategy states follow instruction two first.). However, internal logic can be used to overcome the strategy and follow the instructions independent of the strategy. Moreover, if a strategy is not provided, then the logic can be used to follow the instructions. In addition, the logic can differentiate between various instructions and some instructions could not be followed while others are followed (e.g., logic determines to follow instruction three, but not instruction one.).

Action 1106 is gathering information that relates to an output. Commonly, an output is not information that should be presented, but an indicator as to what information should be presented. Therefore, based on the output, information is gathered. In an illustrative example, an output can disclose that a calendar would be beneficial to disclose. Event 1106 obtains the calendar so it can be presented to a user. However, it is to be appreciated that an output can be information that can be disclosed.

There is presenting gathered information 1108. Presenting can take form through a number of different embodiments, including audio presentation, visual disclosure, physical conveyance (e.g., lifting of marks to present information in Braille), etc. Accumulating information that relates to at least one previous output 1110 can take place. Various reactions can take place in accordance with an output. For instance, a user can be presented with information. In a sample configuration, unless a user makes an explicit action (e.g., send an error report) that presented information was poor (e.g., not beneficial), then an assumption is made that presented information was adequate.

A check 1112 occurs to determine if a presentation is adequate. For instance, a check can configure to determine if an error report was sent. If an error report was not sent during disclosure, the alteration does not take place and a new output for a new presentation can take place (e.g., return to action 1104.) If an error report is received, then the methodology 1100 continues to event 1114.

There is training an artificial neuron network based on accumulated information 1114 (e.g., training based on accumulated information, training based on accumulated information and at least one other factor, etc.) Training allows an artificial neuron network to operate in a more efficient manner, produce higher quality information, etc. According to one embodiment, operational structure of the artificial neuron network is changed (e.g., altering a sequence used by the artificial neuron network.)

Figure 12:
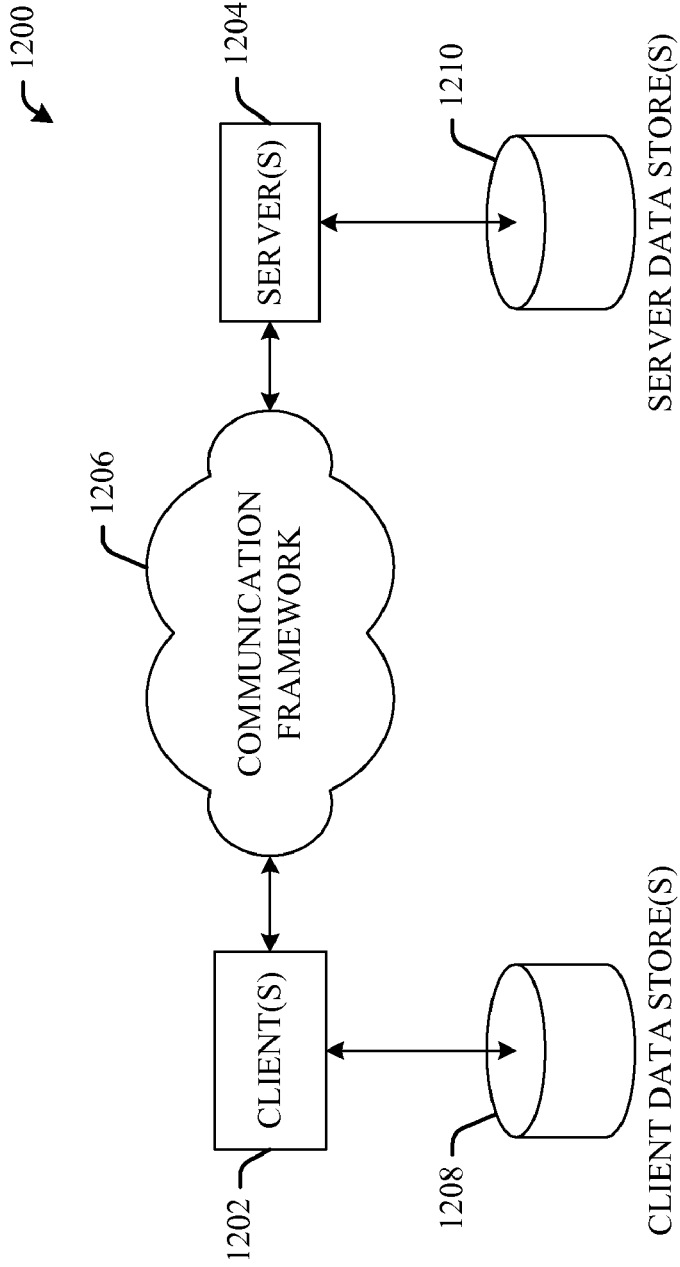
FIG. 12 illustrates an example of a schematic block diagram of a computing environment in accordance with the subject specification.
Figure 13:
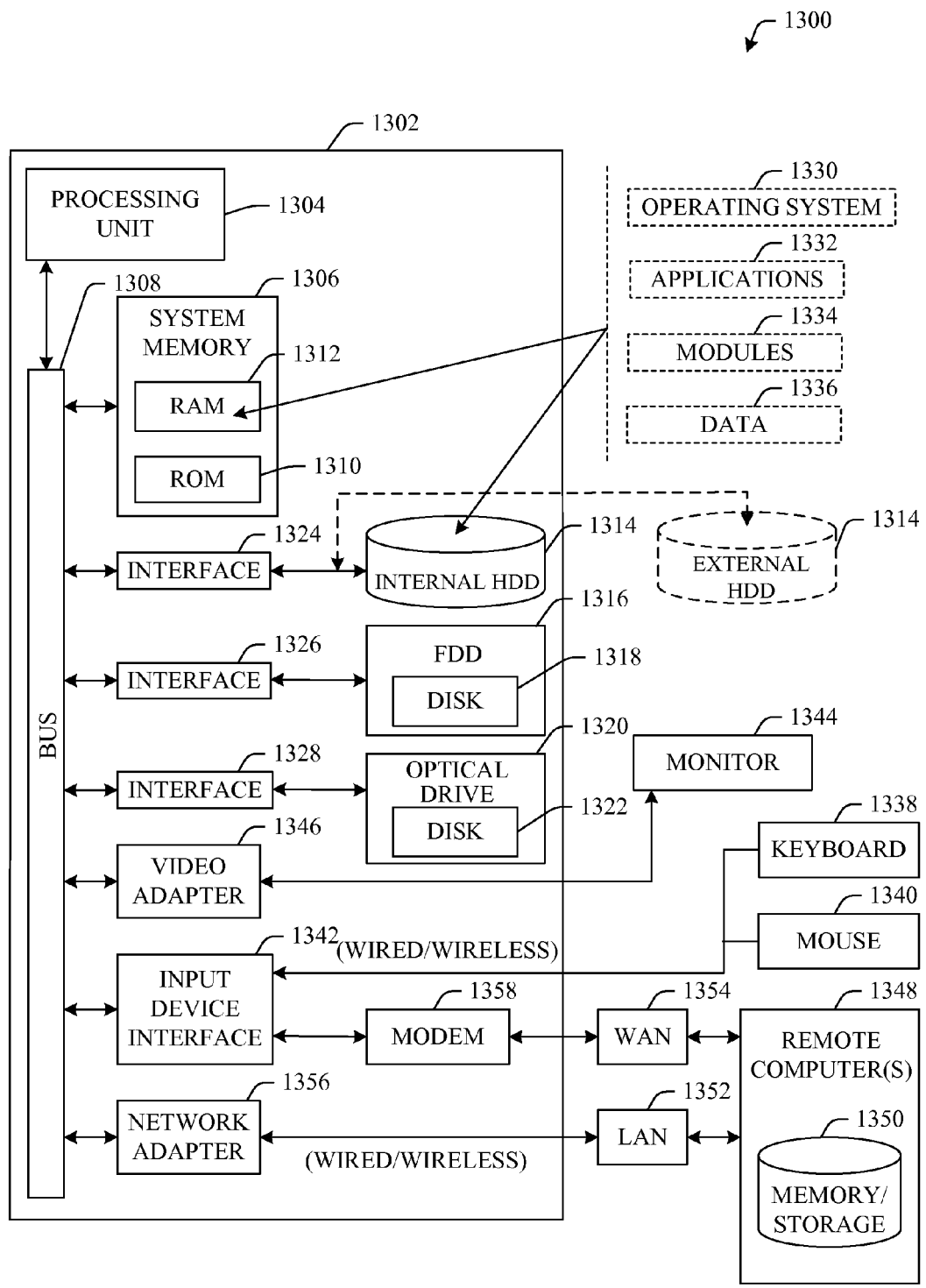
FIG. 13 illustrates an example of a block diagram of a computer operable to execute the disclosed architecture.

In order to provide a context for the various aspects of the disclosed subject matter, FIGS. 12 and 13 as well as the following discussion are intended to provide a brief, general description of a suitable environment in which the various aspects of the disclosed subject matter can be implemented. While the subject matter has been described above in the general context of computer-executable instructions of a program that runs on one or more computers, those skilled in the art will recognize that the subject matter described herein also can be implemented in combination with other program modules. Generally, program modules include routines, programs, components, data structures, etc. that perform particular tasks and/or implement particular abstract data types. Moreover, those skilled in the art will appreciate that the inventive methods can be practiced with other computer system configurations, including single-processor, multiprocessor or multi-core processor computer systems, mini-computing devices, mainframe computers, as well as personal computers, hand-held computing devices (e.g., personal digital assistant (PDA), phone, watch . . . ), microprocessor-based or programmable consumer or industrial electronics, and the like. The illustrated aspects can also be practiced in distributed computing environments where tasks are performed by remote processing devices that are linked through a communications network. However, some, if not all aspects of the claimed subject matter can be practiced on stand-alone computers. In a distributed computing environment, program modules can be located in both local and remote memory storage devices.

Referring now to FIG. 12, there is illustrated a schematic block diagram of a computing environment 1200 in accordance with the subject specification. The system 1200 includes one or more client(s) 1202. The client(s) 1202 can be hardware and/or software (e.g., threads, processes, computing devices). The client(s) 1202 can house online-based cookie(s) and/or associated contextual information by employing the specification, for example.

The system 1200 also includes one or more server(s) 1204. The server(s) 1204 can also be hardware and/or software (e.g., threads, processes, computing devices). The servers 1204 can house threads to perform transformations by employing the specification, for example. One possible communication between a client 1202 and a server 1204 can be in the form of a data packet adapted to be transmitted between two or more computer processes. The data packet can include a cookie and/or associated contextual information, for example. The system 1200 includes a communication framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s) 1208 that can be employed to store information local to the client(s) 1202 (e.g., cookie(s) and/or associated contextual information). Similarly, the server(s) 1204 are operatively connected to one or more server data store(s) 1210 that can be employed to store information local to the servers 1204.

Referring now to FIG. 13, there is illustrated a block diagram of a computer operable to execute the disclosed architecture. In order to provide additional context for various aspects of the subject specification, FIG. 13 and the following discussion are intended to provide a brief, general description of a suitable computing environment 1300 in which the various aspects of the specification can be implemented. While the specification has been described above in the general context of computer-executable instructions that can run on one or more computers, those skilled in the art will recognize that the specification also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the specification can also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 13, the example environment 1300 for implementing various aspects of the specification includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures can also be employed as the processing unit 1304.

The system bus 1308 can be any of several types of bus structure that can further interconnect to a memory bus (with or without a memory controller), a peripheral bus, and a local bus using any of a variety of commercially available bus architectures. The system memory 1306 includes read-only memory (ROM) 1310 and random access memory (RAM) 1312. A basic input/output system (BIOS) is stored in a non-volatile memory 1310 such as ROM, EPROM, EEPROM, which BIOS contains the basic routines that help to transfer information between elements within the computer 1302, such as during start-up. The RAM 1312 can also include a high-speed RAM such as static RAM for caching data.

The computer 1302 further includes an internal hard disk drive (HDD) 1314 (e.g., EIDE, SATA), which internal hard disk drive 1314 can also be configured for external use in a suitable chassis (not shown), a magnetic floppy disk drive (FDD) 1316, (e.g., to read from or write to a removable diskette 1318) and an optical disk drive 1320, (e.g., reading a CD-ROM disk 1322 or, to read from or write to other high capacity optical media such as the DVD). The hard disk drive 1314, magnetic disk drive 1316 and optical disk drive 1320 can be connected to the system bus 1308 by a hard disk drive interface 1324, a magnetic disk drive interface 1326 and an optical drive interface 1328, respectively. The interface 1324 for external drive implementations includes at least one or both of Universal Serial Bus (USB) and IEEE 1394 interface technologies. Other external drive connection technologies are within contemplation of the subject specification.

The drives and their associated computer-readable media provide nonvolatile storage of data, data structures, computer-executable instructions, and so forth. For the computer 1302, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, can also be used in the example operating environment, and further, that any such media can contain computer-executable instructions for performing the methods of the specification.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. It is appreciated that the specification can be implemented with various commercially available operating systems or combinations of operating systems.

A user can enter commands and information into the computer 1302 through one or more wired/wireless input devices, e.g., a keyboard 1338 and a pointing device, such as a mouse 1340. Other input devices (not shown) can include a microphone, an IR remote control, a joystick, a game pad, a stylus pen, touch screen, or the like. These and other input devices are often connected to the processing unit 1304 through an input device interface 1342 that is coupled to the system bus 1308, but can be connected by other interfaces, such as a parallel port, an IEEE 1394 serial port, a game port, a USB port, an IR interface, etc.

A monitor 1344 or other type of display device is also connected to the system bus 1308 via an interface, such as a video adapter 1346. In addition to the monitor 1344, a computer typically includes other peripheral output devices (not shown), such as speakers, printers, etc.

The computer 1302 can operate in a networked environment using logical connections via wired and/or wireless communications to one or more remote computers, such as a remote computer(s) 1348. The remote computer(s) 1348 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1350 is illustrated. The logical connections depicted include wired/wireless connectivity to a local area network (LAN) 1352 and/or larger networks, e.g., a wide area network (WAN) 1354. Such LAN and WAN networking environments are commonplace in offices and companies, and facilitate enterprise-wide computer networks, such as intranets, all of which can connect to a global communications network, e.g., the Internet.

When used in a LAN networking environment, the computer 1302 is connected to the local network 1352 through a wired and/or wireless communication network interface or adapter 1356. The adapter 1356 can facilitate wired or wireless communication to the LAN 1352, which can also include a wireless access point disposed thereon for communicating with the wireless adapter 1356.

When used in a WAN networking environment, the computer 1302 can include a modem 1358, or is connected to a communications server on the WAN 1354, or has other means for establishing communications over the WAN 1354, such as by way of the Internet. The modem 1358, which can be internal or external and a wired or wireless device, is connected to the system bus 1308 via the serial port interface 1342. In a networked environment, program modules depicted relative to the computer 1302, or portions thereof, can be stored in the remote memory/storage device 1350. It will be appreciated that the network connections shown are example and other means of establishing a communications link between the computers can be used.

The computer 1302 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the subject specification. It is, of course, not possible to describe every conceivable combination of components or methodologies for purposes of describing the subject specification, but one of ordinary skill in the art can recognize that many further combinations and permutations of the subject specification are possible. Accordingly, the subject specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
    an artificial neuron network configured to create an output that is at least in part an estimation of information appropriateness for presentment;
    a reception component configured to obtain at least one output of the artificial neuron network and transmit a confirmation of receipt of the at least one output;
    a gather component configured to select data for presentment based upon received output of the artificial neuron network;
    a disclosure component configured to present data selected by the gather component, the disclosure component including at least a processor and internal logic configured to determine a resolution at which to present an image, and further including a modification component configured to alter at least a level of detail in the data selected by the gather component based on an importance of the data;
    a train component configured to modify the artificial neuron network based on the at least one output of the artificial neuron network, and on active and passive feedback obtained via the disclosure component, and further configured to compare an estimated output of the artificial neuron network against an actual output of the artificial neuron network to determine a rate of error relating to operation of the artificial neuron network;
    an evaluation component configured to determine a context of factors to be considered by the artificial neuron network, as a basis for determining a relative importance of the factors; and
    a formulation component configured to create a strategy for use by the artificial neuron network based on the context and relative importance of the factors determined by the evaluation component.

2. The system of claim 1, wherein the artificial neuron network is configured to obtain information from at least storage and sensors.

3. The system of claim 2, wherein the artificial neuron network is a three-layer feed-forward model.

4. The system of claim 1, wherein the train component is further configured to receive instructions via a connection to a terminal.

5. The system of claim 1, further comprising an analysis component configured to evaluate at least one piece of information used by the artificial neuron network to create an output.

6. The system of claim 1, further comprising a transmission component configured to emit the artificial neuron network to an auxiliary location.

7. The system of claim 1, further comprising a timer component configured to determine when presentment of selected data is beneficial, based at least in part on a comparison between a time when the artificial neuron network predicted information to be beneficial and a time when the information is actually beneficial.

8. The system of claim 1, wherein the disclosure component includes at least one of a monitor, a printer or a speaker system.

9. The system of claim 1, further comprising artificial intelligence configured to make at least one inference or at least one determination or at least one of each in relation to selection of data.

10. The system of claim 1, wherein data selected by the gather component is fetched or presented prior to a request for the data.

11. The system of claim 1, wherein output of the artificial neuron network relates at least in part to a condition.

12. The system of claim 1, further comprising storage configured to hold at least one piece of profile information used by the artificial neuron network to generate an output.

13. A method, comprising:
   accumulating information that relates to at least one previous output of an artificial neuron network;
   training the artificial neuron network based at least in part on the accumulated information, and on active and passive feedback associated with the accumulated information;
   presenting the accumulated information at an altered level of detail based on determining an importance of the accumulated information;
   comparing an estimated output of the artificial neuron network against an actual output of the artificial neuron network to determine a rate of error relating to operation of the artificial neuron network;
   determining a context of factors to be considered by the artificial neuron network, as a basis for determining a relative importance of the factors; and
   creating a strategy for use by the artificial neuron network based on the determining of the context and relative importance of the factors.

14. The method of claim 13, further comprising establishing a time constraint with respect to operation of the artificial neuron network.

15. The method of claim 14, further comprising determining, based on the time constraint, whether presenting the accumulated information is beneficial.

16. The method of claim 15, further comprising comparing a time when the artificial neuron network predicted the accumulated information to be beneficial and a time when the accumulated information is actually beneficial.

17. The method of claim 14, further comprising collecting information from at least one of storage or a sensor.

18. The method of claim 13, further comprising transferring the trained artificial neuron network to a supplemental position.

19. The method of claim 13, further comprising accumulating information based on the comparing.

20. A computer-readable storage medium storing instructions to perform a method according to claim 13.

* * * * *